United States Patent [19]
Goodman et al.

[11] Patent Number: 5,166,141
[45] Date of Patent: Nov. 24, 1992

[54] IMMUNOSTIMULATING 7-DEAZA-7-OXA- AND 7-DEAZA-7-OXO-ANALOGS OF 8-SUBSTITUTED-GUANINE-9-(1′-BETA-D-ALDOGLYCOSIDYL) DERIVATIVES AND METHODS OF TREATING TEST ANIMALS

[75] Inventors: Michael G. Goodman, Rancho Santa Fe, Calif.; Edward P. Gamson, Highland Park, Ill.

[73] Assignee: Scripps Clinic and Research Foundation, La Jolla, Calif.

[21] Appl. No.: 198,141

[22] Filed: May 24, 1988

Related U.S. Application Data

[63] Continuation-in-part of Ser. No. 798,629, Nov. 15, 1985, Pat. No. 4,746,651, which is a continuation-in-part of Ser. No. 546,679, Nov. 1, 1983, Pat. No. 4,643,992.

[51] Int. Cl.$^5$ .................. A61K 31/70; C07H 19/167; C07H 19/173
[52] U.S. Cl. ........................ 514/45; 536/24; 536/26; 536/22
[58] Field of Search ............. 514/45, 48; 536/24; 424/85.8

[56] References Cited

U.S. PATENT DOCUMENTS

| | | | |
|---|---|---|---|
| 3,161,654 | 12/1964 | Shen | 548/500 |
| 3,228,831 | 1/1966 | Nicholson et al. | 514/568 |
| 3,313,848 | 4/1967 | Scherrer et al. | 562/454 |
| 3,385,886 | 5/1968 | Nicholson et al. | 562/492 |
| 3,466,372 | 9/1969 | Shen et al. | 514/62 |
| 3,530,113 | 9/1970 | Rossi | 536/4.1 |
| 3,538,077 | 11/1970 | Rossi | 536/4.1 |
| 3,542,761 | 11/1970 | Rossi | 536/4.1 |
| 3,600,437 | 8/1971 | Marshall | 562/465 |
| 3,641,127 | 2/1972 | Farge et al. | 562/426 |
| 3,654,349 | 4/1972 | Shen et al. | 562/428 |
| 3,767,805 | 10/1973 | Carney et al. | 514/429 |
| 3,849,572 | 11/1974 | Witzel et al. | 514/522 |
| 3,993,755 | 11/1976 | Kulbakh et al. | 514/43 |
| 4,486,436 | 12/1984 | Sunshine et al. | 514/263 |
| 4,746,651 | 5/1988 | Goodman | 514/45 |
| 4,880,784 | 11/1989 | Robins et al. | 514/48 |

OTHER PUBLICATIONS

Nagahara, K., et al., J. Med. Chem., vol. 33, pp. 407–415.
Parandoosh, Z., et al., Biochem. Biophys. Res. Comm., vol. 163, pp. 1306–1311, 1989.
Smee, D., et al., Antimicrobial Agents and Chemotherapy, vol. 33, pp. 1487–1492, 1989.
The Handbook of Chemistry and Physics, R. C. Weast, ed., CRC Press, Cleveland (1973) p. C-46.

*Primary Examiner*—Johnnie R. Brown
*Assistant Examiner*—L. Eric Crane
*Attorney, Agent, or Firm*—Dressler, Goldsmith, Shore, Sutker & Milnamow, Ltd.

[57] ABSTRACT

An immune response-enhancing guanosine analog derivative having a structure that conforms to the formula

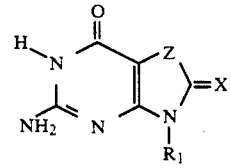

wherein Z is oxygen (O) or sulfur (S); X is oxygen (O), sulfur (S) selenium (Se) or cyanimino (NCN); and $R_1$ is an aldoglycoside is disclosed. Also disclosed are a composition containing the guanosine analog derivative as active ingredient and a method of using the composition for immunostimulation.

7 Claims, No Drawings

IMMUNOSTIMULATING 7-DEAZA-7-OXA- AND 7-DEAZA-7-OXO-ANALOGS OF 8-SUBSTITUTED-GUANINE-9-(1'-BETA-D-ALDOGLYCOSIDYL) DERIVATIVES AND METHODS OF TREATING TEST ANIMALS

CROSS-REFERENCE TO COPENDING APPLICATION

This is a continuation-in-part of copending application Ser. No. 798,629 filed Nov. 15, 1985, now U.S. Pat. No. 4,746,651, and which was a continuation-in-part of application Ser. No. 546,679, filed Nov. 1, 1983, now U.S. Pat. No. 4,643,992.

DESCRIPTION

1. Technical Field

The present invention relates to immune response enhancing compounds (immunostimulants), and more particularly to guanine nucleoside derivatives that are substituted at the 7- and 8-positions of the guanine ring, as well as to compositions containing those derivatives and methods of their use.

BACKGROUND OF THE INVENTION

An animal's immune system is comprised of numerous elements that act separately and/or in concert to counteract, to eliminate, or to neutralize substances that are recognized by that system as foreign to the animal host. Generally, but not necessarily, the substance recognized as foreign by the immune system has its origin exogenous to the host. Exemplary of such exogenous substances are infectious bacteria and the by-products of their cellular activity, virus particles and their proteins, proteins injected by insect stings, and the like. In autoimmune diseases, such as rheumatoid arthritis, the host's immune system recognizes host-made proteins or self-made proteins as foreign.

The principal effectors of the immune system are the leukocytes, which include lymphocytes of thymic origin (T cells), lymphocytes produced in bone marrow (B cells), neutrophils which, inter alia, produce enzymes that make oxidizing agents such as hydrogen peroxide that have cytotoxic effects upon bacteria, and macrophages which present the foreign substance or antigen to the T cells, as well as produce a protein designated interleukin-1 that assists T cell transformation into T helper cells. Complement which is a complex mixture of proteins that acts in an ordered, cascading manner upon the foreign substance also plays a major role in immune responses.

B cells can be distinguished from T cells, inter alia, by the presence of immunoglobulins on their membrane surfaces. The immunoglobulins function as antibodies.

There are five known classes of immunoglobulins, identified as IgA, IgD, IgE, IgG, and IgM on the basis of five antigenically different heavy chain proteins which in part make up the immunoglobulin molecule. B cells also bear non-immunoglobulin cell markers, including a complement receptor (CR), a receptor for the Fc portion of immunoglobulin (FCR), I-region associated antigens (Ia), and a set of differentiation antigens (Lyb 1-7) which are identified by all antisera and are correlated with various aspects of B cell maturation and activation. These markers are useful in phenotypically identifying B cells.

While the B cell immunoglobulins act upon the foreign substance, or antigen, the T cells, and particularly helper T cells, are believed necessary to stimulate B cells to divide and to differentiate into antibody secreting cells for humoral immunity. Suppressor T cells contribute to the regulation of humoral immunity, while cytotoxic T cells and T cell mediators of delayed-type hypersensitivity are the principal effectors of cell mediated immunity.

T cells include antigens designated CD4 and CD8 that are related to T cell functions. Helper T cell precursors are of the CD4+, CD8− phenotype. It is these cells which normally participate in the activation and regulation of B cells.

Helper T cells are known to assist in activation and differentiation of immunoglobulin-secreting B cells after a first message is received by the B cells from the activating antigenic agent. However, the mode by which the T cells provide the second message for B cell proliferation (or activation) and differentiation to the B cells is a matter of controversy.

Guanosine-3',5'-cyclic monophosphate (cGMP) has been implicated as a naturally occurring agent for providing the required second message for B cell proliferation. 8-Bromoguanosine-3',5'-cyclic monophosphate (8-BrcGMP) has been found to be a weak synthetic intracellular lymphocyte mitogen.

The immune response can be modified by artificial supression (immunosuppression) or enhancement (immunopotentiation or immunostimulation). Immunosuppression; i.e., artificially induced decreased responsiveness, can be achieved by six general methods: (1) administration of antigen, (2) administration of specific antisera or antibody, (3) use of other biologic reagents such as antilymphocyte antisera, (4) use of drugs or hormones, (5) radiation, and (6) surgical removal of lymphoid tissue. Immunopotentiation can include the administration of an agent effecting an increase in the rate at which the immune response develops, an increase in the intensity or level of the response, a prolongation of the response, or the development of a response to an otherwise non-immunogenic substance.

The agents that are known to enhance immune responses are generally termed adjuvants and can be placed into two general categories: (1) those providing general potentiation; i.e., substances that enhance both cellular and humoral immune responses for a wide variety of antigens, and (2) those providing specific potentiation, i.e., substances which enhance specific responses to certain antigens only.

Substances that can act as adjuvants can be grouped into the following categories: (1) water and oil emulsions, e.g., Freund's adjuvant, (2) synthetic polynucleotides, (3) hormones, drugs and cyclic nucleotides, (4) endotoxins, (5) proteinaceous lymphokines and monokines such as the interleukins.

A substance capable of specifically potentiating the immune response is transfer factor, a dialyzable leukocyte extract (DLE) obtained from human peripheral leukocytes. It has been reported that the transfer factor exhibits some effectiveness in patients with immunodeficiencies and possible effectiveness in cancer patients and in patients with limited immunodeficiencies. However, much remains to be learned about this particular substance.

In some diseases and physiological conditions such as AIDS, X-linked agammaglobulinemias, senescence and drug-induced-immunosuppression, B cell activation and differentiation is lacking and/or exists only at a reduced level, thereby lessening the immune response of the host. These diseases and conditions are representative of immunosuppressed states. Here, enhanced activation and differentiation, if it can be effected, tends to beneficially lessen the disease manifestation and/or improve the patient's condition.

An immunopotentiated state can be illustrated by the bodily condition after vaccination. Here, the immune response is already enhanced due to an antigenic response, but could be beneficially enhanced still further to provide an improved degree and/or duration of immunity.

Co-assigned U.S. Pat. No. 4,539,205 to Goodman and Weigle describes modulation of animal cellular responses with 8-substituted guanine derivatives bonded 9-1' to an aldose having 5 or 6 carbon atoms in the aldose chain (ring). The cellular modulations described in that patent relate mostly to immunomodulation such as adjuvanticity in producing primary and secondary immune responses. Activity against certain neoplastic conditions is also disclosed as are T cell-replacing activity, an IL-1 like activity on thymocytes, and induction of the release of lysosomal enzymes from neutrophils. The 8-substituents in those molecules have electron withdrawing inductive effects relative to hydrogen. Thus, halo, mercapto or its thioxo tautomer, acyl mercapto, alkyl sulfido, nitro, cyano, keto, halomethyl and methyleneoxy alkyl and the like were disclosed as useful, while electron donating substituents such as an amino group were found to be inactive.

In addition, co-assigned U.S. Pat. No. 4,643,992 and its corresponding published European patent application No. 83306791.1 further disclose the use of derivatives of 8-hydroxyguanine (8-oxoguanine), 7-methyl-8-oxoguanine and 7-methyl-8-thioxoguanine in modulating animal cellular responses. Further results using guanine derivatives disclosed in U.S. Pat. No. 4,539,205 are disclosed in U.S. Pat. No. 4,643,992, as are similar results using guanine derivatives disclosed for the first time in that patent.

Still further, several papers and book chapters have been published by some of the present inventors and their co-workers disclosed and claimed in U.S. Pat. No. 4,643,992. Exemplary of those published papers are Goodman, *Proc. Soc. Exp. Biol. Med.*, 179:479 (1985); Goodman, *J. Immunol.*, 136:3335 (1986); Goodman and Weigle in *Purine Metabolism In Man, Part B*, Nyhan and Thompson, eds., Plenum Press, New York, page 451 and 443 (1986); Goodman and Weigle, *J. Immunol.*, 135:3284 (1985); Goodman, *J. Immunol.*, 136:3335 (1986); Goodman, *J. Immunol.*, 137:3753 (1986); and Goodman and Hennen, *Cell. Immunol.*, 102:395 (1986).

BRIEF SUMMARY OF THE INVENTION

The present invention contemplates compounds, compositions utilizing a compound, and methods using such a composition. The compounds are 7-deaza-7-oxa- or 7-deaza-7-thia-analogs of 8-substituted-guanine-9-(1'-beta-D-aldoglycosidyl) derivatives, aldoglycosidyl O-substituted lower alkyl, lower alkylidene, lower alkanoyl, benzyl and benzoyl derivatives, and their pharmaceutically acceptable, non-toxic base addition salts. The compounds have a structure that corresponds to Formula I, below.

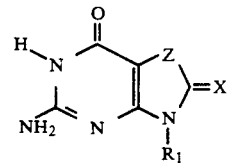

wherein Z is oxygen (O) or sulfur (S); X is oxygen (O), sulfur (S), selenium (Se) or cyanimino (NCN); and $R_1$ is an aldoglycoside or derivative that is described hereinafter, as well as the pharmaceutically acceptable, non-toxic base addition salts thereof.

Animal immune responses are enhanced by contacting leukocytes in an aqueous medium with a composition containing a diluent amount of a physiologically tolerable carrier admixed with an effective amount of a compound of the invention. The contact between the cells and the composition is maintained for a period of time sufficient for the contacted leukocytes to manifest enhancement of their immune response.

Enhancement of immunogen(antigen)-specific humoral immune responses resulting in adjuvanticity that provides enhanced antibody secretion in the presence of immunogen, is a particular example of an immune response that can be enhanced in accordance with the present invention.

An immune response-enhancing composition of this invention can be used to provoke differing, although related results depending, inter alia, upon the manner of administration, dosage and the cell population to which it is administered. The active ingredient guanosine analog derivative is present in the composition admixed in the carrier as a suspension of solid guanosine analog derivative in a solid or liquid carrier, or as a dissolved solute in the carrier.

Contacting leukocytes such as B lymphocytes with a composition of this invention and maintaining that contact for a predetermined period of time enhances the immune response of those leukocytes. Enhancement of B lymphocyte (B cell) responses can be effected by treating B cells with an effective amount of the immunogen to form immunogen-primed B cells, followed by contacting the B cells with the immune response-enhancing composition and a further effective amount of immunogen. B cell immune responses can also be modulated by contacting the B cells with a priming immunogen and an immune response-enhancing composition of this invention followed thereafter by contacting those cells with an additional effective amount of the immunogen alone, or with a further amount of immune response-enhancing composition. In addition, an immune response-enhancing composition can be administered to contact the animal cells and thereafter followed, while the guanosine analog derivative is in contact with the animal cells; i.e., present in vivo or in vitro, with one or more immunizing doses of an immunogen. These immune response enhancements are within those effects referred to as adjuvanticity; i.e., the guanosine analog derivative acts as an adjuvant for the immunogen, and thus provides an immunogen- or antigen-specific modulation.

The methods of this invention can be used on cells in vivo as well as in vitro to cell cultures. The compositions can be administered subcutaneously, intravenously intraperitoneally in a liquid form, or perorally as in pill or capsule form, or in liquid form as a slurry, suspension or solution.

The present invention has several benefits and advantages.

One benefit of the present invention is that its compounds are effective in providing an enhanced response at a given dose.

An advantage of the invention is that use of one of its compositions can provide the second message required for B lymphocyte activation and differentiation in response to a first (antigenic) message.

Another benefit of the invention is that an enhanced immune response can be effected in both the presence and absence of T helper cell activity. Thus, an enhanced immune response is noted in both T cell-dependent and T cell-independent systems.

Another advantage of this invention is that particular immune-suppressed or immune-deficient conditions and disease manifestations can be improved and/or lessened by use of the invention.

Still further benefits and advantages of the invention will be apparent to those skilled in the art from the discussion that follows.

Anthropomorphic descriptions such as the sending and receiving of messages by and to chemicals and cells are used herein for descriptive purposes as aids to the understanding of observed phenomena.

DETAILED DESCRIPTION OF THE INVENTION

I. Introduction

The present invention contemplates an immune response-enhancing agent (immunostimulator) that stimulates the immune system of the host mammal to which it is administered as well as stimulating leukocytes in cell culture. The immunostimulation particularly contemplated is predominantly antigen-specific for the immunizing antigen.

In studying the effects of some reportedly mitogenic guanosine derivatives, e.g., guanosine 3′,5′-cyclic monophosphate and its 8-bromo derivative, it was found that a new class of low molecular weight guanine nucleoside derivatives, when present in an effective amount as the active ingredient of a composition containing a diluent amount of a physiologically tolerable carrier, provided remarkable effects in modulating responses of mammalian cells. Enhancement of antigen-specific humoral immune responses, which resulted in potent adjuvanticity, T cell replacing factor-like activity and immunoreconstitution activity are particular examples of the cellular responses that were found to be modulated. Those compounds and their methods of use are disclosed in U.S. Pat. Nos. 4,539,205 and No. 4,643,992.

II. The Compounds

7-thia- and 7-deaza-7-oxa-analogs of 8-substituted-guanosine Derivatives

1. Guanosine Analogues

A compound of the present invention is a derivative of an analog of guanine. Guanine is itself a purine derivative that has a structure that corresponds to formula II, below, wherein the numerals identify ring numbering positions.

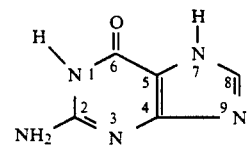

A compound of the present invention contains an oxygen or sulfur atom (0 or S) substituted for the 7-position imino nitrogen of a guanine, and therefore can be referred to as a guanine analog. Such compounds can also be referred to as 7-deaza-7-oxa- and 7-deaza-7-thiaguanines, respectively.

A compound of the present invention also contains a divalent radical (=O, =S, =Se or =N—CN) substituted for the hydrogen (H) at the 8-position of guanine, and further includes an aldoglycoside bonded to the 9-position. A guanine analog bonded 9,1′-beta to a ribosyl group can be referred to as a guanosine analog derivative.

The phrase "guanosine analog derivative" is used herein generically to include compounds that have aldoglycoside radicals in place of ribosyl radicals, as well as those that contain ribosyl radicals. Specific compounds are given appropriate names.

2. Aldoglycosides

The 9-aldoglycoside portion ($R_1$) of the useful guanosine analog derivatives are cyclic, contain 5 or 6 carbon atoms, and are selected from the group consisting of 1′-aldopentosidyl, 1′-aldohexosidyl, mono-deoxygenated-1′-aldopentosidyl, and mono-deoxygenated-1′-aldohexosidyl radicals. The useful aldoglycosides are bonded to the 9-position of the guanine analog, respectively, and are of the D configuration. The aldoglycosides are free from electric charge at physiological pH values and are therefore free from carboxy, phosphate and quaternary ammonium substituents.

Exemplary 1′-aldopentosidyl radicals are the 1′-radicals of ribose, arabinose, lyxose and xylose that are named 1′-ribofuranosidyl, 1′-arabinofuranosidyl, 1′-lyxofuranosidyl, and 1′-xylofuranosidyl radicals, respectively. Exemplary 1′-aldohexosidyl radicals are the 1′-radicals of glucose, galactose, mannose, gulose, allose, altrose, and rhamnose that are named 1′-glucopyranosidyl, 1′-galactopyranosidyl, 1′-mannopyranosidyl 1′-gulopyranosidyl, 1′-allopyranosidyl, 1′-altropyranosidyl, 1′-rhamnopyranosidyl, radicals, respectively. An exemplary mono-deoxygenated 1′-aldopentosidyl radical is that of deoxyribose that is named the 1′-(2′-deoxy)-ribofuranosidyl radical. An exemplary mono-deoxygenated 1′-aldohexosidyl radical is that of deoxyglucose, named the 1′-(2′-deoxy)glucopyranosidyl radical.

Useful aldoglycosidyl radicals can have one or more hydroxyl groups esterified by a lower alkanoyl radical such as formyl, acetyl, propionyl or hexanoyl (lower alkanoyloxy radicals), and also by a benzoyl radical. Aldoglycosidyl radicals are also useful when esterified by lower alkyl, especially methyl and ethyl radicals (lower alkoxy), benzyl radicals, and lower alkylidene radicals. 2′-Deoxyaldoglycosides are also useful as esters and ethers.

Suitable aldoglycosidyl radicals conform to the formula

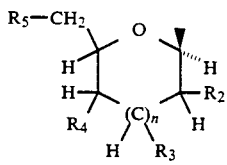

wherein n is one or zero, such that when n is zero the =CHR$_3$ group is absent and the aldoglycoside is an aldopentosidyl radical, whereas when n is one, the aldoglycoside is an aldohexosidyl radical;

R$_2$ is hydrogen, hydroxy, lower alkoxy such as methoxy, ethoxy and the like, benzyloxy, lower alkanoyloxy such as formyloxy, acetoxy (and the like, or benzoxy.

R$_3$ when present, as well as R$_4$ and R$_5$, all are preferably the same. These radicals can be hydroxy, a lower alkyl ether (lower alkoxy) such as methoxy and ethoxy, a benzyl ether (benzyloxy), a lower alkanoyl radical (lower alkanoyloxy) such as formyloxy, acetoxy, or a benzoate ester (benzoxy). When R$_2$ is other than hydrogen, it is preferred that R$_2$=R$_3$ (when present)=R$_4$=R$_5$. Thus, an O-substituent, (when present on one oxygen is preferably present on all available ring substituent oxygens.

In another embodiment, when n=0 (R$_3$ is absent) and R$_2$ and R$_4$ are in a cis configuration, as in ribose, R$_2$ and R$_4$ can together form a lower alkylidenedioxy radical. A lower alkylidenedioxy radical is a ketal or acetal formed from a lower alkyl (C$_1$-C$_6$) ketone or aldehyde, respectively. A particularly preferred lower alkylidenedioxy radical is formed from acetone and is referred to as isopropylidene. When R$_2$ and R$_4$ together form a lower alkylidenedioxy radical, R$_5$ is preferably hydroxy, lower alkanoyloxy or benzoxy.

As used herein, the term "lower" used in conjunction with "lower alkoxy", "lower alkyl", "lower alkanoyloxy" or "lower alkanoyl" relates to a C$_1$-C$_6$ alkyl derivative. Lower alkoxy radicals include methoxy, ethoxy, iso-propoxy, cyclopentoxy, hexyloxy and the like, whereas lower alkanoyloxy radicals include formyloxy, acetoxy, propionyloxy, butanoyl, cyclopentanoyloxy, hexanoyloxy, and the like.

The bonds of the above formula are not intended to convey any particular stereo specific configuration, except at the 1'-position at which the beta anomer is indicated, and that the D form of the aldoglycoside is contemplated.

In preferred practice, the aldoglycosidyl radical is selected from the group consisting of 1'-ribofuranosidyl, 1'-glucopyranosidyl, and 1'-(2'-deoxy)ribofuranosidyl radicals. Thus, preferably, when n is zero and R$_2$, R$_4$ and R$_5$ are all hydroxy, R$_3$ is absent, the aldoglycosidyl radical is selected from the group consisting of 1'-ribofuranosidyl; when n is zero, R$_2$ is hydrogen and R$_4$ and R$_5$ are hydroxy, R$_3$ is absent, the aldoglycosidyl radical is 2'-deoxy-1'-ribofuranosidyl; and when n is 1, and R$_2$=R$_3$=R$_4$=R$_5$=hydroxy, 1'-glucopyranosidyl is an aldoglycosidyl radical.

As already noted, the aldoglycoside is bonded from its 1'-position to the 9-position of a guanosine analog derivative. When named as a guanosine analog derivative, that bonding can be described as a 9-1' bond. The beta anomer of the aldoglycoside is that preferred herein, although mixtures of alpha and beta anomers are also useful.

3. Exemplary Immune Response-Enhancing Agents

Structural formulas of exemplary immune response-enhancing agents of the invention that are useful in a composition and method of this invention are shown below, wherein X, Z and R$_1$ are as shown in Table 1 following the structural formulas.

TABLE 1

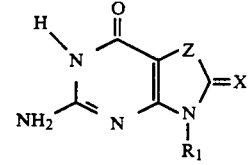

| Z | X | R$_1$ |
|---|---|---|
| O | O | 1'-ribofuranosidyl |
| O | O | 1'-lyxofuranosidyl |
| O | O | 1'-glucopyranosidyl |
| O | O | 1'-(2'-deoxy)ribofuranosidyl |
| S | O | 1'-gulopyranosidyl |
| S | O | 1'-allopyranosidyl |
| S | O | 1'-xylofuranosidyl |
| S | O | 1'-(2',3',4',6'-tetra-O-methyl)gulopyranosidyl |
| S | S | 1'-ribofuranosidyl |
| S | S | 1'-allopyranosidyl |
| S | S | 1'-(2',3',5'-tri-O-benzoyl)-galactopyranosidyl |
| O | S | 1'-mannopyranosidyl |
| O | S | 1'-ribofuranosidyl |
| O | S | 1'-(2',3',4',6'-tetra-O-benzyl)altropyranosidyl |
| O | Se | 1'-ribofuranosidyl |
| O | Se | 1'-lyxofuranosidyl |
| O | Se | 1'-glucopyranosidyl |
| O | Se | 1'-(2'-deoxy)ribofuranosidyl |
| S | Se | 1'-gulopyranosidyl |
| S | Se | 1'-allopyranosidyl |
| S | Se | 1'-xylofuranosidyl |
| S | Se | 1'-(2',3',4',6'-tetra-O-methyl)gulopyranosidyl |
| O | NCN | 1'-ribofuranosidyl |
| O | NCN | 1'-allopyranosidyl |
| O | NCN | 1'-(2',3',5'-tri-O-benzoyl)-galactopyranosidyl |
| O | O | 1'-(2',3'-isopropylidenyl)-ribofuranosidyl |
| S | O | 1'-(2',3'-isopropylidenyl)-ribofuranosidyl |

The 8-substituent of 7-deaza-7-oxa- and 7-deaza-7-thiaguanosine analog derivatives is preferably oxo, whereas a 7-deaza-7-oxaguanosine analog derivative is preferred over a 7-deaza-7-thiaguanosine analog derivative.

Particularly preferred compounds include 7-deaza-7-oxa-8-oxoguanosine or 7-deaza-7-oxa-8-oxo-9-(1'-beta-D-ribofuranosidyl)guanine; 7-deaza-7-oxa-8-oxo-9-(1'-beta-D-2'-deoxyribofuranosidyl)guanine; 7-deaza-7-oxa-8-oxo-9-(1'-beta-D-glucopyranosidyl)guanine; 7-deaza-7-thia-8-oxoguanosine or 7-deaza-7-thia-8-oxo-9-(1'-beta-D-ribofuranosidyl)guanine; 7-deaza-7-thia-8-oxo-9-(1'-beta-D-2'-deoxyribofuranosidyl)guanine; and 7-deaza-7-thia-8-oxo-9-(1'-beta-D-glucopyranosidyl)-guanine.

A useful guanosine analog derivative is substantially free from ionic charge at physiological pH values; i.e., about pH 7.0 to about pH 7.5, except for the ionic charges that might be provided by the relatively acidic 1-position ring nitrogen atom. Thus, a useful molecule is free of acid and base-containing moieties that are not present in guanosine. That freedom from acidic and basic groups extends from the $R_1$ radical, and throughout the whole guanosine molecule.

The guanosine analog derivatives are acids, and as such can form base addition salts. Such salts are useful in providing storage stability and do not provide an added ionic charge to a guanosine analog derivative used in a method of the invention because of the buffering effect provided by the host's blood and lymph systems or the buffer of a culture medium.

Pharmaceutically acceptable, non-toxic base addition salts of guanosine analog derivatives are useful herein, and can be formed by treatment of the immune response-enhancing agent with an appropriate base, in a suitable solvent such as water or a lower alkyl alcohol such as methanol or ethanol. Exemplary inorganic bases include sodium hydroxide, potassium hydroxide, ammonium hydroxide and the like. Exemplary organic bases include tris-(hydroxymethyl)aminomethane (TRIS), 4-(2-hydroxyethyl)-1-piperazine-ethanesulfonic acid (HEPES) and the like bases. Conversely, the base addition salt form can be converted to the free guanosine form by treatment with acid.

4. Syntheses

The substituted guanosine analog derivatives useful herein are readily prepared by procedures analogous to those published in the chemical literature. Exemplary syntheses are provided hereinafter in the Materials and Methods Section.

Those exemplary reactions follow the course of reaction Schemes I and II that are pictured below. It is noted that abbreviated structures are utilized in those schemes for added clarity in presentation. However, those abbreviated structures are well known by those skilled in the art of organic synthesis.

In addition, the reaction closing the 5-membered ring to form an 8-oxo or 8-thioxo derivative is shown for the oxo derivative with the reagent for forming the thioxo substituent shown in parentheses. Once the 5-membered ring is shown as closed, the sulfur atom, S, that could alternatively occupy the 8-position is shown in brackets.

Still further, compounds whose synthesis are not specifically discussed in the Materials and Methods section are either commercially available or their syntheses are discussed in one or more publications.

Scheme I

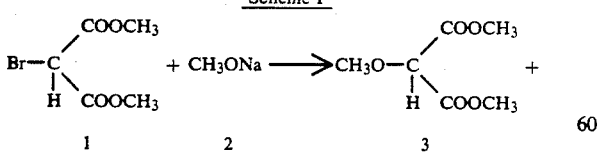

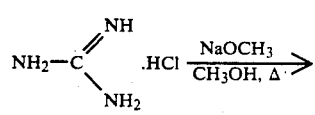

-continued
Scheme I

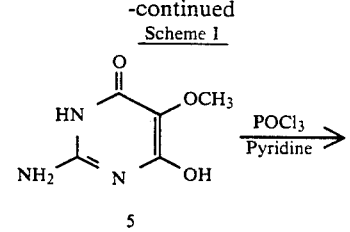

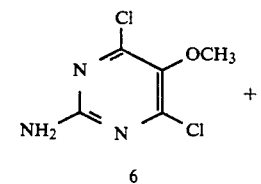

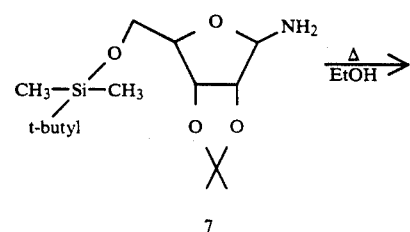

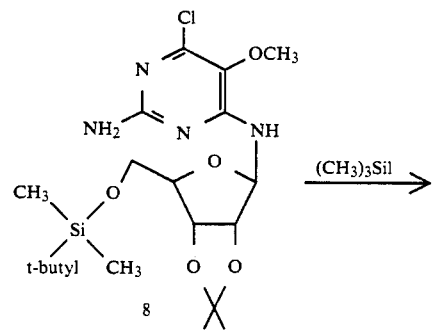

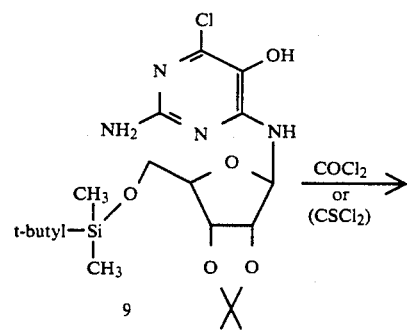

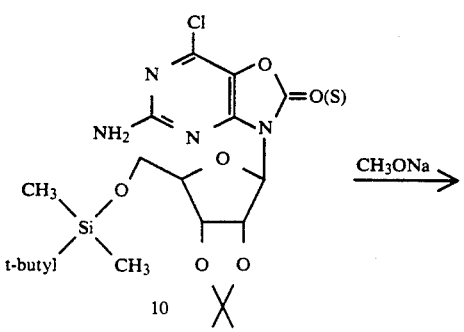

5,166,141
11
-continued
Scheme I
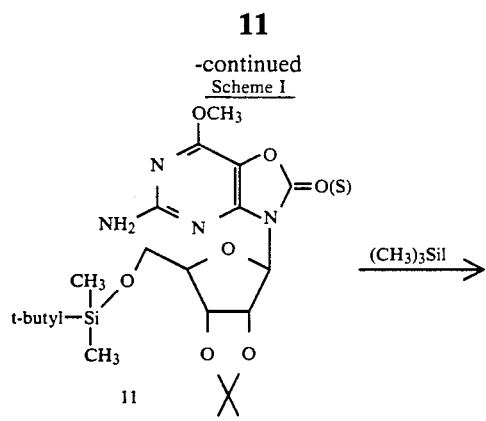
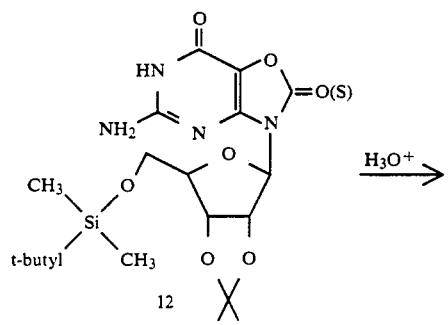
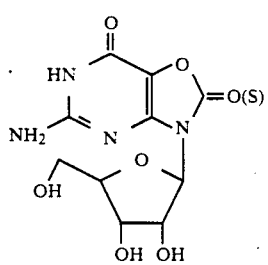
13
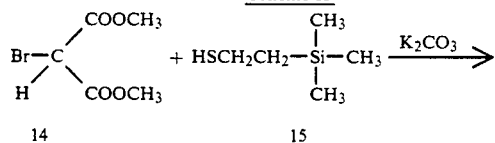
Scheme II
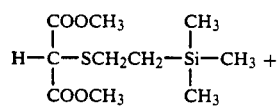
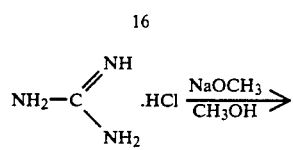
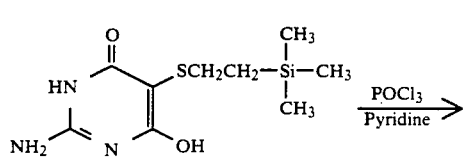
12
-continued
Scheme II
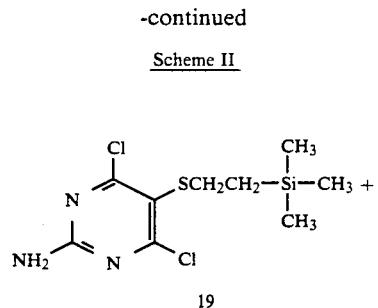
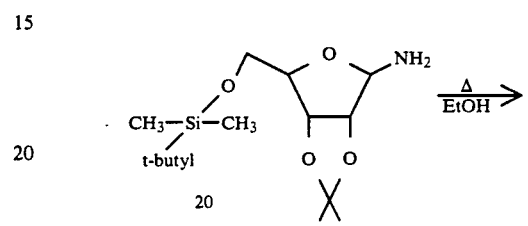
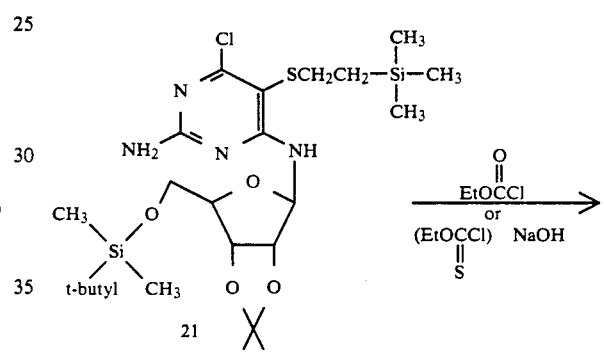
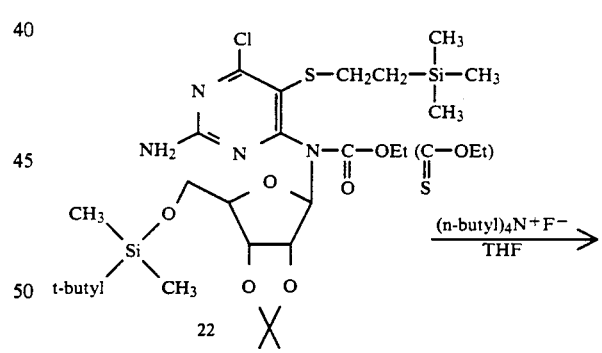
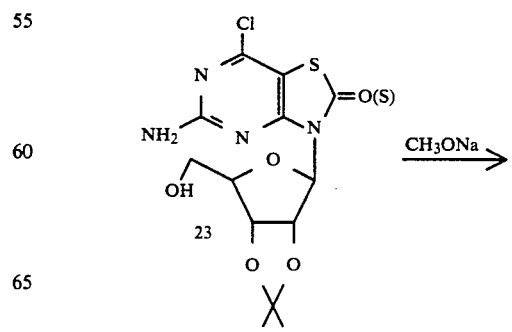

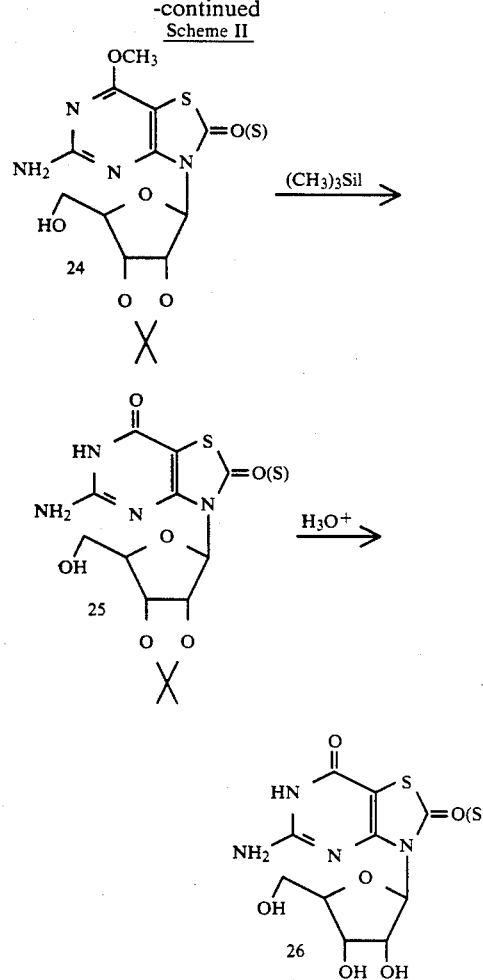

-continued
Scheme II

Δ = heat to reflux;
t-butyl = tertiary-butyl;

$\diagup\!\!\!\!\diagdown^O_O$ = isopropylidenedioxy;

Et = ethyl;
EtOH = ethanol;
THF = tetrahydrofuran; and
nBu = normal butyl.

The 8-selenoxo and 8-cyanimino derivatives are prepared from the corresponding 8-thioxo derivatives. Here, the 8-thioxo compound is first alkylated as with methyl iodide, and the thionium salt so formed is thereafter reacted with sodium selenide or with cyanamide and sodium hydride to form the respective 8-selenoxo or 8-cyanimino derivatives.

III. The Compositions

A composition of this invention comprises a diluent amount of a physiologically tolerable carrier (also referred to herein as a vehicle or diluent) admixed with an immunopotentiating (immune response-enhancing or immunostimulating) effective amount of a guanosine analog derivative or salt of this invention described before.

A composition for in vivo administration is typically provided for per oral or parenteral administration in customary unit dosage compositions. The term "unit dosage" and its grammatical equivalents as used herein refer to physically discrete units suitable as unitary dosages for human patients and other mammals, each unit containing a predetermined effective amount of the guanosine analog derivative active ingredient calculated to produce the desired therapeutic effect in association with the required physiologically tolerable carrier, e.g. a diluent or a vehicle. The specifications for the novel unit dosage forms of this invention are dictated by and are directly dependent on (a) the unique characteristics of the active guanosine derivative ingredient and the particular therapeutic effect to be achieved, and (b) the limitations inherent in the art of compounding such an active ingredient for therapeutic use in vitro, as well as in vivo in humans and other animals.

Examples of suitable unit dosage forms in accord with this invention are tablets, capsules, pills, powder packets, granules, wafers, and the like, segregated multiples of any of the foregoing, as well as liquid solutions, emulsions and suspensions. Liquid compositions can be administered in usual manners such as subcutaneously, intraperitoneally, intramuscularly, perorally or the like.

The amount of active ingredient that is administered in vivo as an effective immunostimulating amount depends on the age and weight of the patient, the particular condition to be treated, the frequency of administration, and the route of administration. The total daily dose range can be about 0.01 to about 200 milligrams per kilogram of body weight, more preferably about 0.1 to about 25 milligrams per kilogram of body weight, and most preferably about 1 to about 15 milligrams per kilogram of body weight. The human adult dose is in the range of about 5 to about 1400 milligrams daily, given either as a single dose or in 3 or 4 divided doses. Veterinary dosages correspond to human dosages with the amounts administered being in proportion to the weight and metabolic rate of the animal as compared to adult humans.

It will be appreciated by those skilled in the art that useful in vivo concentrations can vary from animal species to animal species. Those skilled workers also know that appropriate concentrations can be readily determined.

Concentrations for the in vitro contacting of animal cells are about $1\times 10^{-6}$ molar to about $3\times 10^{-4}$ molar for cell concentrations of about $10^6 - 10^7$ cells per milliliter. More preferably, the concentration is about $1\times 10^{-5}$ molar to about $1\times 10^{-4}$ molar. The peak concentration; i.e., the concentration that provides the greatest adjuvanticity, for a given guanosine analog nucleoside can vary when studied in mouse and human lymphocyte systems.

A composition can be a solid or a liquid. Physiologically tolerable carriers are well known in the art. Exemplary of liquid carriers are sterile aqueous solutions that contain no materials in addition to the active ingredient guanosine derivative and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes. The latter carriers are exemplified by Ringer's Injection, Dextrose Injection, Dextrose and Sodium Chloride Injection and Lactated Ringer's Injection.

Liquid compositions can also contain liquid phases in addition to and to the exclusion of water. Exemplary of such additional phases are glycerin, vegetable oils, such as cotton seed oil, sesame oil and water-oil emulsions.

Exemplary solid carriers include those materials usually used in the manufacture of pills or tablets, and include corn starch, lactose, dicalcium phosphate, thickeners such as tragacanth gum and methylcellulose U.S.P., finely divided $SiO_2$ polyvinylpyrrolidone, magnesium stearate and the like. Additionally, the solid carrier can include biodegradable and non-biodegradable polymers, polypeptide carriers, affinity carriers such as AFFI-GEL 601 (phenyl boronate resin available from BIO-RAD Laboratories, Richmond, Calif.), liposomes and synthetic polymers, as are known in the art. Antioxidants such as methylparaben and propylparaben can be present in both solid and liquid compositions, as can sweeteners such as cane or beet sugar, sodium saccharin, sodium cyclamate and the dipeptide aspartic-phenylalanine methyl ester sweetener sold under the tradename NUTRASWEET (aspartame) by G. D. Searle Co.

IV. Method of Immunostimulation

A method of enhancing the immune response of leukocytes is also contemplated. Preferably, the immune response is an antigen-specific response. In accordance with this method, leukocytes such as lymphocyte preparations, B cells, T cells, neutrophils and macrophages are contacted separately or in combination in an aqueous medium with a before-described composition containing an immunostimulating effective amount of a before-described guanosine analog derivative.

The method can be practiced in vivo in humans, laboratory mammals such as mice, rats and guinea pigs or in veterinary animals and pets such as pigs, horses, cattle, dogs and cats. The method can also be practiced in vitro in cell cultures such as in hybridoma culture for the production of monoclonal antibodies.

The leukocytes are contacted in an aqueous medium regardless of whether the composition of guanosine analog derivative is itself a solid or liquid, or whether or not the liquid of the composition is aqueous. For the in vivo method, the aqueous medium is supplied at least in part by the water of the blood or lymph. For in vitro methods, the aqueous medium is supplied at least in part by the culture medium used.

Contact between the composition and leukocytes is maintained for a time period sufficient for the contacted cells to manifest the enhancement of their immune response. That immunostimulation can itself be manifest in cellular proliferation, enhanced antibody secretion, enhanced T helper activity, enhanced cytokine production from T cells and macrophages, enzyme secretion from neutrophils, and the like.

An antigen-specific response of B cells is a usual and preferred result of immunoenhancement. Additional illustrative antigen-specific immunoenhancements that can be achieved using a method of the invention include enhanced proliferation of T cells, the in vitro reconstitution of the primary immmune response in immunodeficient B cells, T cell-replacing activity in B cells, and an in vivo enhancement of antibody production, enhanced T helper cell activity, and increased cytokine secretion.

For use in vivo, contact between leukocytes and a composition is typically maintained for a time period sufficient for the animal to clear the guanosine analog derivative from its body as by metabolism, excretion or both processes. That time period can be longer than that required for immunostimulation to be manifest. Contact with an individual unit dose is typically maintained for a time period of hours to about a week or more, depending, for a given compound, upon the carrier or vehicle used. Continual contact can be advantageous for an immunodeficient animal host.

Contact in vitro can be maintained for a period of time sufficient for one of the before-described immunostimulations to become manifest as determined by standard assay techniques such as a plaque-forming assay for B cells. Such maintenance times typically take about one to about seven days of time, and more usually about 2 to about 6 days.

V. Treatments

A. In Vitro Adjuvanticity

Contacting animal antibody-producing cells with a composition useful herein provides an adjuvant effect on the primary antibody response to SRBC and other immunogens when evaluated in vitro. The immune response-modulating composition and effective amount of immunogen (sheep red blood cells; SRBC) are typically admixed to contact the cells substantially simultaneously. The words "antigen" and "immunogen" are used interchangeably.

At optimal concentration, a composition containing an effective amount of a useful guanosine analog derivative enhances the response to SRBC by at least about 2-to 6-fold. The effect is dose dependent. Enhancement of the antibody response cannot be accounted for by the additive effects of the specific response to SRBC and the polyclonal response to the guanosine analog derivative.

The adjuvant effect of compositions containing a useful guanosine analog derivative is exerted on immunogen-experienced (primed) as well as on naive cells. Both responses are enhanced by contacting the cells with compositions containing an effective amount of guanosine analog derivative. This adjuvant effect is dependent upon the concentration of immunogen added to culture. Thus, the primary IgM as well as the secondary IgM and IgG responses to immunogen (antigen) are augmented by contacting B cells with a composition containing an effective amount of an guanosine analog derivative as active ingredient, and maintaining that contact as discussed herein.

While immune responses; i.e., responses of B lymphocytes or B cells, are observed to be enhanced at all immunologically effective doses of immunogen, the degree of enhancement is usually greatest at optimal or near optimal immunogen concentrations. Additionally, adjuvanticity of guanosine analog derivatives is synergistic with immunogen and not just due to the sum of independent immunogen-specific and polyclonal (non-specific) responses.

For memory responses, B cells are primed by treatment with an effective, priming, amount of an immunogen, as is well known. That priming treatment can be in the presence or absence of an immune response-modulating composition. When contacted in the presence of such a composition, treatment of the B cells with a priming amount of immunogen is preferably substantially simultaneous; i.e., within about 12 hours, with contacting of the cells with a composition useful in this invention. More preferably, the immunogen is included in the immune response-enhancing composition, unless its effect is impaired by being in that composition, as by denaturation.

In summary, an enhanced immune response can thus be obtained by contacting B cells substantially simultaneously with an effective, priming amount of immunogen and an immune response-enhancing composition useful herein, followed, after a primary immune response is obtained, by an additional contacting of the primed cells with a further effective amount of immunogen (antigen) alone or substantially simultaneously with a further amount of immune response-enhancing composition.

Guanosine analog derivative-containing compositions useful herein are thought to enhance the primary humoral immune response by acting directly upon the B cell and/or the immunogen-presenting cell. Thus, use of these derivatives enhances the antibody response mounted against T-independent antigens; i.e., responses that involve B cells and immunogen-presenting cells. In addition, compositions containing an guanosine analog derivative can replace the need of B cells for T helper cells, as discussed hereinafter, and therefore exert their adjuvant effect in cultures initiated in the absence of intact, functional T cells. A replacement of T cells with T cell helper activity contained in mixed lymphocyte culture (MLC) supernates does not diminish the ability of an guanosine analog derivative to augment the antibody response.

Still further, the synergy observed between the soluble T cell signal contained in MLC supernate and the guanosine analog derivative-containing composition indicates that the signal supplied by each is qualitatively distinct. This synergy is observed over a range of supernate concentrations, indicating that the guanosine analog derivative is not simply providing more of the same "signal" that T cells provide. A comparable degree of synergy can be observed when such B cell cultures are supplemented with T cells rather than with T cell-like supernates (which are in fact T cell derived), and are contacted in the presence of immunogen with an guanosine analog derivative-containing composition useful in this invention.

T cell-mediated effects of the adjuvanticity of guanosine analog derivatives are not ruled out by the observation of T-independence for that adjuvanticity; i.e., the existance of a T cell-independent facet does not bear upon the existance of a T cell-dependent phase. Thus, more substantial enhancement can be observed from a composition containing the guanosine analog derivative under conditions of stimulation with low doses of T-dependent and T-independent type 2 antigens (T cell dependent situations) than with T-independent type 1 antigens (more completely T cell-independent), which suggests the presence of a T cell-dependent component. Moreover, guanosine analog derivatives are thought to act (either directly or indirectly) on precursors of T helper cells to increase the ability of a population of such cells to support (i.e., help) an antibody response to immunogen.

B. In Vivo Enhancement Of Immune Response

Immunopotentiating effects on the primary antibody (B cell) response to SRBC in vivo are observed when a liquid composition containing a guanosine analog derivative useful herein is contacted with animal cells as by injecting the composition into CBA/CaJ mice about thirty minutes after injection of the SRBC immunogen; i.e., substantially simultaneously. Relatively high dosages, e.g., about 2.5 milligrams per animal (about one-tenth gram per kilogram), are tolerated by the animals.

Immunogen dose dependency is observed in the above mice in the presence or absence of adjuvant. A much higher response level is seen in animals injected i.p. with a guanosine analog derivative compared with normal saline (NS) i.p. injections as a control. Whereas there is an enhancement in the immune response at all useful (effective) levels of immunogen injection, typically, the enhancement becomes greater as the magnitude of the underlying response increases.

In vivo enhancement of animal cellular responses as in the above-described primary immunization can also be effected as described before in relation to in vitro modulation of secondary immune responses of B cells.

CBA/CaJ mice are immunized intraperitonally (i.p.) using a conjugate (TNP-BSA) prepared by the reaction of 2,4,6-trinitrobenzene sulfonic acid (TNBS) and bovine serum albumin (BSA) in a 0.28 molar cacodylate buffer, at pH 6.9. Each animal receives an intraperitoneal (i.p.) injection containing 50 micrograms (ug) of the immunizing conjugate. One group of mice thereafter (within about 30 minutes) receives another i.p. injection that contains a guanosine analog derivative of the invention in either 100 percent sesame seed oil or an aqueous composition containing 2 volume percent sesame oil sonicated with saline. Each animal receives 0.2 ml of the guanosine analog derivative from the compositions each of whose concentration of guanosine analog derivative is 5 mg/ml. A third group of mice receives the immunization but no composition of this invention and serve as a control. Anti-TNP-BSA antibody secretion from each group is thereafter monitored over a period of about 30 days using standard enzyme-linked immunosorbant assay (ELISA) techniques using TNP-BSA as antigen.

The results of such a study indicate that animals receiving a guanosine analog derivative of the invention exhibit enhanced anti-TNP-BSA antibody titers as compared to titers from animals that do not receive the guanosine analog derivative.

C. T Cell-Replacing Activity

A composition of this invention can be used to substitute for T cells in the antibody response to a T-dependent antigen. Here, murine B cells generated in vitro by treatment with monoclonal anti-thy 1.2 plus complement are cultured with or without SRBC as antigen in the presence of compositions containing incremental concentrations of a guanosine analog derivative.

Under these conditions, isolated B cell cultures respond poorly to T-dependent antigens unless supplemented with a guanosine analog derivative of the invention. The guanosine analog derivative-enhanced response is dose-dependent as well as antigen-dependent. Thus, contacting B cells in vitro with a composition of this invention provides a T cell-like signal to those contacted cells.

D. In Vitro Reconstitution of the Primary Humoral Immune Response

CBA/N mice possess an X-chromosome linked (X-linked) primary B cell immunodeficiency, and thereby can provide a murine model for sex-linked immunodeficiency. The CBA/N strain is thought to be deficient in the functional activity of a subpopulation of mature B lymphocytes bearing the Lyb 3/5/7 antigens. See, Huber et al., *J. Exp. Med.*, 145:1(1977); Ahmed et al., *J. Exp. Med.*, 145:101 (1977); and Subbaro, *J. Immunol.*, 122:2279 (1979).

Cultures of spleen cells from male and female homozygous CBA/N mice and male mice heterozygous for the CBA/N gene, called the xid gene, (male mice bear the X chromosome) is prepared as described in the Materials and Methods section. 0.1 Milliters of a 0.1 percent (v/v) SRBC suspension alone or the SRBC suspension plus incremental amounts of a guanosine analog derivative of the invention are added to the cultures, using $5 \times 10^6$ cells/ml. Direct anti-SRBC plaque-forming cultures per culture are assessed after 4 days of culture.

Using a similar preparation of spleen cells from immunocompetent CBA/CaJ mice shows that at the zero guanosine analog derivative concentration level there is substantially no response for the CBA/N cells, as compared to a positive PFC/culture response for the immunocompetent CBA/CaJ cells.

At concentrations of about $10^{-4}-10^{-5}$ molar guanosine analog derivative, both the immunocompetent CBA/CaJ cells and originally immunoincompetent CBA/N cells are made capable of producing significant numbers of PFC/culture. Thus, contacting X-linked immunodeficient splenocytes with a composition of this invention can reconstitute the primary humoral immune response to SRBC of those otherwise immunodeficient cells.

Immunodeficiency in mice as well as other mammals can come from old age or senescence as well as by genetic defect as discussed above. Thus, animals that were immunocompetent as juveniles or adults can become immunodeficient as they reach old age. That is the case for the inbred CBA/CaJ mouse strain.

A further study of the reconstitution of a primary humoral antibody response to SRBC is carried out using spleen cells from senescent, 156-week old, CBA/CaJ mice that have become immunodeficient through age. The in vitro responses of those spleen cells to SRBC in a plaque-forming assay are compared to similar responses from cells of another group of healthy, adult 8-week old, CBA/CaJ mice. This comparison is carried out as described above, again using a composition containing a guanosine analog derivative of the invention to contact the splenocytes.

The PFC/culture for the healthy, adult mice controls containing SRBC but no guanosine analog derivative are several times the number formed in the absence of both SRBC and guanosine analog derivative. The PFC/culture for the controls for the senescent mice are about equal for both controls, and elevated compared to those of healthy adults. Those relatively elevated and similar responses are thought to reflect the process that culminates in formation of autoantibody-producing clones.

A guanosine analog derivative dose-related response is observed in the presence of SRBC. That response is observed for both the immunocompetent healthy adult splenocytes and the previously immunodeficient, but now primary humoral response-reconstituted senescent splenocytes. Such results thereby illustrate that contacting immunodeficient senescent splenocytes with a composition of this invention can reconstitute this deficient immune response.

Having generally described this invention, a further understanding can be obtained by reference to syntheses and procedures that are provided hereinafter below for purposes of illustration.

VI. Materials and Methods

A. Syntheses

In the syntheses described below, compound numbers identified by an underlined numeral correspond to the similarly numbered compounds shown in Schemes I and II. Again, syntheses are discussed here for those compounds that are not commercially available or that are key intermediates in the reaction sequence. Those skilled in the art will be able to produce or purchase the remaining compounds.

Scheme I Preparations

EXAMPLE 1

Preparation of compound 3

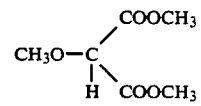

To a solution of sodium methoxide 2 in methanol is added a solution of 1 (1 equivalent; eq.) in CH$_3$OH at zero degrees C. under N$_2$. After addition, the mixture is allowed to warm to room temperature (about 22 degrees C) and stirred for 2 hours. Most of the methanol is removed in vacuo, the residue is treated with water, and extracted with methylene chloride. The organic layer is dried over Na$_2$SO$_4$ and the solvent is removed in vacuo to provide the title compound 3.

EXAMPLE 2

Preparation of compound 5

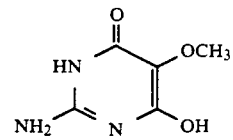

A mixture of 3 and 4 (1.1 eq.), sodium methoxide (1.1 eq.) and methanol is heated to reflux under nitrogen for 16 hours. After cooling, most of methanol is removed in vacuo, and the residue is treated with cold water. The white solid is filtered and washed with cold water to provide the title compound 5.

EXAMPLE 3

Preparation of compound 6

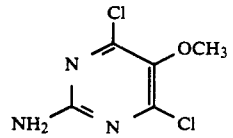

To a mixture of 5, pyridine (20 eq.) and acetonitrile is added POCl$_3$ (5 eq.) at zero degrees C. under N$_2$. After addition, the mixture is heated to reflux for two hours. The mixture is cooled to room temperature, and the solvent is removed in vacuo. The residue is treated with methylene chloride and washed with saturated NaHCO$_3$, then water, and is thereafter dried over Na$_2$SO$_4$. The solvent is removed in vacuo to provide the title compound 6.

EXAMPLE 4

Preparation of compound 8

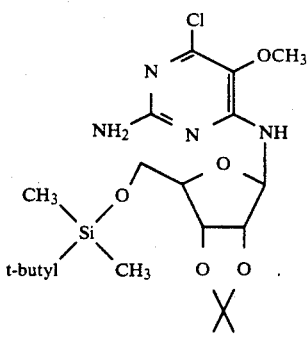

A mixture of 6 (1 eq.), 7 (1 eq.), potassium carbonate and absolute ethanol is heated to reflux under nitrogen for 16 hours. The mixture is cooled to room temperature and filtered. The filtrate is concentrated in vacuo and the residue is purified by column chromatography on silica gel to provide the title compound 8.

EXAMPLE 5

Preparation of compound 9

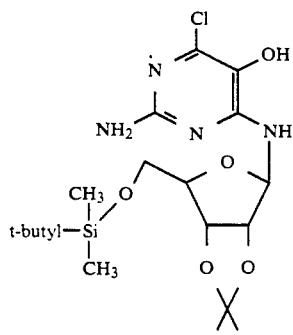

To a solution of 8 (1 eq.) in methylene chloride is added trimethylsilyl iodide (1 eq.) at zero degrees C. under $N_2$, and the resulting mixture is stirred for 3 hours. The mixture is poured into sodium bicarbonate solution. The organic layer is separated and dried over $Na_2SO_4$. The solvent is removed in vacuo and the residue is purified by column chromatography on silica gel to provide the title compound 9.

EXAMPLE 6

Preparation of compound 10

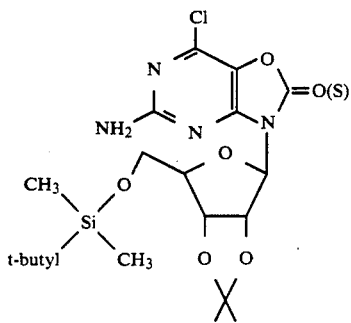

To a mixture of 9 (1 eq.), potassium carbonate (2.5 eq.) and tetrahydrofuran is added a solution of phosgene in xylene (1 eq.) [or thiophosgene (neat) (1 eq.)] at zero degrees C. under nitrogen. After addition, the mixture is allowed to warm to room temperature and stirred for about 18 hours. The mixture is filtered, and the filtrate is concentrated in vacuo. The residue is purified by column chromatography on silica gel to provide the title compound 10.

EXAMPLE 7

Preparation of compound 11

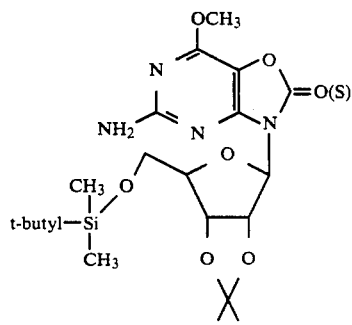

To a solution of 10 (1 eq.) in dimethyl formamide (DMF) is added sodium methoxide (1.1 eq) at zero degrees C. under $N_2$. After addition, the mixture is allowed to warm to room temperature, and stirred for 3 hours. Most of solvent is removed in vacuo and the residue is purified by column chromatography on silica gel to provide the title compound 11.

EXAMPLE 8

Preparation of compound 12

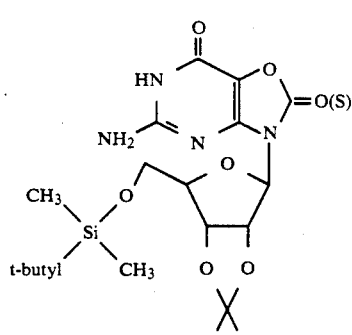

To a solution of 11 (1 eq.) in methylene chloride is added trimethylsilyl iodide (1 eq.) at zero degrees C., and the resulting mixture is stirred for 2 hours. The mixture is poured into dilute sodium bicarbonate solution. The organic layer is separated and dried over $Na_2SO_4$. The solvent is removed in vacuo, and the residue is purified by column chromatography on silica gel to provide the title compound 12.

EXAMPLE 9

Preparation of compound 13

A mixture of 12 (eq.), methanesulfuric acid (catalytic amount) and tetrahydrofuran-water (1:1; v/v) is stirred at room temperature under nitrogen for three days. Most of solvent is removed in vacuo, and the residue is purified by reverse phase HPLC ($C_{18}$-column) to provide the title compound 13.

Scheme II Preparations

EXAMPLE 10

Preparation of compound 16

To a mixture of 15 (1 eq.), $K_2CO_3$ (1.1 eq.) and tetrahydrofuran is added a solution of 14 in tetrahydrofuran at room temperature under nitrogen. The resulting mixture is stirred for 2 hours. Most of solvent is removed in vacuo and the residue is purified by column chromatography on silica gel to provide the title compound 16.

EXAMPLE 11

Preparation of compound 18

The title compound is prepared in a manner analogous to the preparation of compound 5.

EXAMPLE 12

Preparation of compound 19

The title compound is prepared in a manner analogous to the preparation of compound 6.

EXAMPLE 12

Preparation of compound 21

The title compound is prepared in a manner analogous to the preparation of compound 10.

EXAMPLE 14

Preparation of compound 22

To a mixture of 21 (1 eq.), sodium hydroxide pellets and acetonitrile is added ethyl chloroformate (27) [or ethyl chlorothioformate (27')] at zero degrees C. under nitrogen. After addition, the mixture is allowed to warm to room temperature, and is stirred for 3 hours. The resulting mixture is filtered, and the filtrate is concentrated in vacuo. The residue is purified by column chromatography on silica gel to provide the title compound 22.

EXAMPLE 15

Preparation of compound 23

To a solution of 22 (1 eq.) in tetrahydrofuran is added a solution of tetra-n-butylammonium fluoride (2.1 eq.) at zero degrees C., and the resulting mixture is stirred for 3 hours. Most of solvent is removed in vacuo and the residue is purified by column chromatography on silica gel to provide the title compound 23.

EXAMPLE 16

Preparation of compound 24

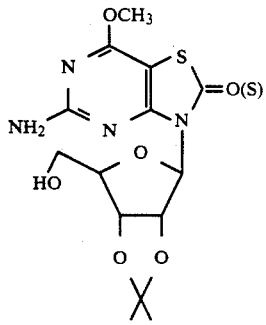

The title compound is prepared in a manner analogous to the preparation of compound 11.

EXAMPLE 17

Preparation of compound 25

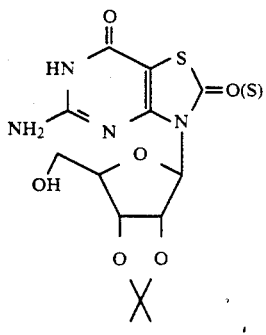

The title compound is prepared in a manner analogous to the preparation of compound 12.

EXAMPLE 18

Preparation of compound 26

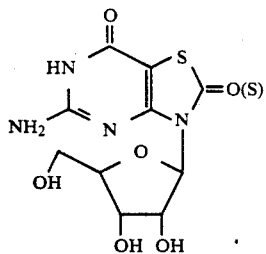

The title compound is prepared in a manner analogous to the preparation of compound 13.

EXAMPLE 19

7-Deaza-7-oxa- or 7-deaza-7-thia-8-selenoxoguanosine Derivatives

7-Deaza-7-oxa- or 7-deaza-7-thia-8-selenoxoguanosine analog derivatives are prepared from suitably protected, corresponding 7-deaza-7-oxa- or 7-deaza-7-thia-8-thioxo derivatives whose preparations are discussed previously. Thus, the 7-deaza-7-oxa- or 7-deaza-7-thia-8-thioxoguanosine is reacted with an S-alkylating agent such as methyl iodide in a solvent such as DMSO. The S-alkylated product so obtained is thereafter reacted with sodium selenide to form the 7-deaza-7-oxa- or 7-deaza-7-thia-8-selenoxo derivative. The desired product can thereafter be obtained from the reaction mixture by reverse phase HPLC.

EXAMPLE 20

7-Deaza-7-oxa- or 7-deaza-7-thia-8-cyanoiminoguanosine Derivatives

Corresponding 7-deaza-7-oxa- or 7-deaza-7-thia-8-thioxoguanosine derivatives are utilized as the starting materials for these derivatives. In a typical preparation, methyl iodide [42 millimoles (mM)] is added to 28 mM of the starting 8-thioxoguanosine analog derivative dissolved in dimethyl sulfoxide (DMSO). The addition takes place at room temperature and under nitrogen. The resulting admixture is stirred for about three hours and then cooled to about zero degrees C. Cyanamide (about 57 mM) is added followed by sodium hydride (60% oil dispersion; 5mM). That reaction mixture is permitted to warm to room temperature and is stirred for about one hour.

The reaction mixture is then poured into about 1.5 liters of diethyl ether and stirred for about 10 minutes. The ether layer is decanted, the residue extracted with a further 1.5 liters of diethyl ether additionally containing about 50 ml of acetic acid. The ether layer is again decanted and the residue is dissolved in water (about 500 ml). The desired compound is purified from the water layer by reverse phase HPLC (C-18).

EXAMPLE 21

Lower Alkylidenedioxy Derivatives

A lower alkylidenedioxy derivative of one of the before-described compounds is exemplified by the following synthesis of an isopropylidene derivative.

A mixture of 7-deaza-7-oxa-8-oxoguanosine (17 mM), 2,2-dimethoxypropane (41 mM), acetone (200 ml) and concentrated sulfuric acid (10 drops) are stirred under $N_2$ at ambient room temperature for a time period of 52 hours. The mixture is cooled to zero degrees C.and treated with concentrated ammonium hydroxide (5 ml). The majority of the liquid is removed in vacuo, and the resulting solid is filtered. The filtered solid is washed with water, acetone, and then diethyl ether, followed by drying in a vacuum oven at 60 degrees C.to provide the desired derivative. Similar procedures are followed for the 8-thioxo, 8-selenoxo and 8-cyanoimino derivatives.

EXAMPLE 22

7-Deaza-7-oxa- or 7-deaza-7-thia-8-oxo-2',3'-O-isopropylidene-5'-benzoylguanosine A mixture containing an isopropylidene derivative as described in Example 21 (3mM), triethylamine (3 ml), benzoyl chloride (3 mM) and methylene chloride (100 ml) is stirred at ambient room temperature for a period of 16 hours. The mixture is thereafter poured into water, the methylene chloride layer separated, and the water layer extracted further with methylene chloride (2×150 ml).

The methylene chloride layers are combined, dried over $NaSO_4$, and the solvent is removed in vacuo. The residue is purified by column chromatography on silica gel.

5'-Acetyl derivatives are prepared by substituting acetic anhydride for benzoyl chloride. 8-Thioxo, 8-selenoxo and 8-cyanimino derivatives are similarly prepared.

EXAMPLE 23
7-Deaza-7-oxa- or 7-deaza-7-thia-8-thioxo-2',3',5'-triacetylguanosine This preparation is exemplary of acylation procedures for the aldoglycosidyl portion of the molecule such as a ribosyl ring. Here, 4-N,N-dimethylaminopyridine (10 mg) is added to a mixture of the 7-deaza-7-oxa- or 7-deaza-7-thia-8-thioxoguanosine (3 mM), triethylamine (2 ml), acetic anhydride (15 mM; lower acyl chlorides or benzoyl chloride can be used in the alternative to prepare the corresponding tri-lower acyl or tribenzyoyl derivatives) and methylene chloride (50 ml). The resulting reaction mixture is stirred under $N_2$ for 16 hours at room temperature.

Further methylene chloride (50 ml) is thereafter added, and the solution is washed with 1N HCl, brine, and then water. The solution is thereafter dried over $Na_2SO_4$. The solvent is removed in vacuo, and the residue is purified by column chromatography on silica gel.

Similar procedures are followed for the 8-oxo, 8-selenoxo and 8-cyanimino derivatives.

B. Exemplary Compositions For Administration

Exemplary solid and liquid compositions suitable for administering the compounds of the present invention are described below using five of the more preferred guanine nucleoside derivatives as exemplary active ingredients.

Tablets

Tablets are compounded from the following ingredients:

|  | Parts by Weight |
|---|---|
| 7-Deaza-7-oxa-8-oxoguanosine | 2.5 |
| Lactose, powdered | 36.4 |
| Corn starch, dry | 34.5 |
| Finely divided $SiO_2$ | 5.6 |
| Polyvinylpyrrolidone | 0.6 |
| Magnesium stearate | 0.4 |
|  | 80.0 |

The guanosine analog derivative is thoroughly admixed with the lactose, 25.0 parts by weight of the corn starch, and 4.0 parts by weight of the $SiO_2$. The resulting admixture is then uniformly moistened with a 5% ethanolic solution of polyvinylpyrrolidone. The moist mass is then passed through a one-millimeter mesh screen to produce a granulate. The produced granulate is dried for about 24 hours at 60° C. in a drying chamber. The dried granulate is again passed through a one-millimeter mesh screen. 70.0 Parts of the obtained granulate are admixed in a suitable mixer with a mixture consisting of the remainder of the $SiO_2$, the remainder of the corn starch and all of the magnesium stearate, which mixture previously had been passed through a one-millimeter mesh screen. The thus-obtained admixture is then pressed into tablets weighing 800 milligrams each and containing 25 milligrams of the guanosine analog derivative.

Starch Capsules

Capsule contents are compounded from the following ingredients:

|  | Parts by Weight |
|---|---|
| 7-Deaza-7-oxa-8-oxo-9-(1'-beta-D-2'-deoxyribofuranosidyl)guanosine | 10.0 |
| Lactose | 450.0 |
| Corn Starch | 540.0 |
|  | 1000.0 |

The guanosine analog derivative is gradually admixed with the lactose. When all of the lactose has been admixed, the obtained admixture is blended with the corn starch. The resulting blend is then filled into capsules holding 10 gram of the blend. Each capsule contains 1.0 milligram of the guanosine analog derivative.

Tablets

A lot consisting of 10,000 tablets, each containing 50 milligrams of 7-deaza-7-oxa-8-oxo-9-(1'-beta-D-glucopyranosidyl)guanosine is prepared from the following types and amounts of ingredients:

| 7-Deaza-7-oxa-8-oxo-9-(1'-beta-D-glucopyranosidyl)guanosine | 500 grams |
|---|---|
| Dicalcium Phosphate | 1000 grams |
| Methyl cellulose, U.S.P. (15 cps) | 75 grams |
| Talc | 150 grams |
| Corn Starch | 250 grams |
| Magnesium stearate | 25 grams |
|  | 2000 grams |

The guanosine analog derivative and dicalcium phosphate are mixed well, granulated with 7.5 percent solution of methyl cellulose in water, passed through a No. 8 screen (U.S. Standard Sieve Series) and dried carefully. The dried granules are passed through a No. 12 screen (U.S. Standard Sieve Series), mixed thoroughly with the talc, starch and magnesium stearate, and compressed into tablets.

Injectable Preparation

A sterile preparation suitable for subcutaneous or intracavitary injection and containing 50 milligrams of 7-deaza-7-thia-8-oxoguanosine in each milliliter of ingredients is prepared from the following types and amounts of ingredients:

| 7-Deaza-7-thia-8-oxoguanosine | 5 grams |
|---|---|
| Physiological saline | 98 milliliters |
| Sesame oil | 2 milliliters |

The guanosine analog derivative and saline are admixed and sonicated for a period of time sufficient to provide a substantially homogenous dispersion. The sesame oil is thereafter admixed and the new admixture is similarly homogenized to provide an emulsion. After emulsification, five to fifteen percent of the final volume of this sterile preparation are injected subcutaneously or intraperitoneally once a week to enhance humoral immunity.

Aqueous Preparation for Oral Use

An aqueous preparation for oral use containing in each 5 milliliters (1 teaspoon) 25 milligrams of 7-deaza-7-thia-8-oxo-9-(1'-beta-D-2'-deoxyribofuranosidyl)guanine is prepared from the following ingredients:

| | |
|---|---|
| 7-Deaza-7-thia-8-oxo-9-(1'-beta-D-2'-deoxyribofuranosidyl)guanine | 5.0 grams |
| Methylparaben, U.S.P. | 0.75 grams |
| Propylparaben, U.S.P. | 0.25 grams |
| Saccharin sodium | 1.25 grams |
| Cyclamate sodium | 0.25 grams |
| Glycerin | 300 milliliters |
| Tragacanth powder | 1.0 grams |
| Orange oil flavor | 1.0 grams |
| F.D. and C. orange dye | 0.75 grams |
| Deionized water, q.s. to | 1000 milliliters |

C. Methods

Lymphocyte cultures. The serum-containing culture medium is prepared to contain the following per 100 milliliters: 91.9 milliliters RPMI 1640 (Flow Laboratories, Inc., Rockville, Md.), 0.1 milliliters of 100 × glutamine, 1.0 milliliter of 100 × sodium pyruvate, 1.0 milliliter of 50 × nonessential amino acids, 1.0 milliliter of water containing $10^4$ units of penicillin G and $10^4$ micrograms of streptomycin, and 5.0 milliliters of a supportive lot of fetal calf serum (FCS). These ingredients are admixed to apparent homogeneity. Spleen cell suspensions and populations enriched for splenic B cells are prepared as described in Goodman et al., *J. Immunol.*, 121:1905 (1978).

For evaluation of the primary humoral immune response to sheep erythrocytes (SRBC), $5 \times 10^6$ to $10^7$ murine spleen cells are cultured in 1.0 milliliter of 5% FCS-containing medium for 4 or 5 days in the presence of immunogen. Cells are incubated in culture trays (Costar, Cambridge, Ma.) at 37° C. in a humidified atmosphere of 10% $CO_2$ in air using tissue culture boxes (CBS Scientific, Del Mar, Calif.) that are rocked at a frequency of 7 cycles per minute. Pooled SRBC are available from the Colorado Serum Co., Denver Colo.

Human peripheral blood lymphocytes (PBL) are prepared from normal heparinized venous blood by Ficoll-diatrizoate density gradient centrifugation. PBL are depleted of suppressor T cells bearing the histamine type 2 receptor by adhering them to the surfaces of histamine-rabbit serum albumin-coated plastic petri dishes (Cell-ect No. 2 kit; Seragen, Boston, Ma.) and by recovering the nonadherent cells by panning as described by Wysocki and Sato, *Proc. Natl. Acad. Sci. USA*, 75:2844 (1978) and modified by Cavagnaro and Osband, *Biotechniques*, January/February:30 (1983).

The tissue culture medium employed in these studies is prepared as follows: One hundred milliliters (ml) contained 87.9 ml RPMI 1640 (Flow Laboratories, Rockville, Md.), 0.1 ml 100 × glutamine, 1.0 ml of 1.0 M HEPES buffer (Microbilogical Associates, Betheseda, Md.), 1.0 ml of water containing $10^4$ U of penicillin G and $10^4$ micrograms of streptomycin, and 10 ml of fresh autologous heat-inactivated plasma. For evaluation of the primary humoral immune response to SRBC, lymphoid cells are cultured at a density of $2 \times 10^6$/ml in a volume of 1.0 ml containing $5 \times 10^6$ SRBC as antigen (Colorado Serum Co., Denver Colo.) together with IL-2 (a partially purified preparation of human IL-2 that is free of interferon-gamma activity is obtained from Electro-Nucleonics, Inc., Silver Spring, Md.) and the guanosine analog derivative.

Assay of plaque forming cells (PFC)

PFC secreting antibodies against SRBC are evaluated after 4 or 5 days of culture using a modification of the hemolytic plaque assay of Jerne and Nordin, *Science*, 140:405 (1963). The cells are brought up in complete medium before plaquing; they are plaqued in standard low $M_r$ agarose (Bio-Rad Laboratories, Richmond Calif.), and are incubated in SRBC-absorbed guinea pig complement for one hour after a 1.5 hour incubation without complement.

T Cell Replacing Activity $5 \times 10^6$ Viable CBA/CaJ mouse B cells are cultured. These cells are generated by sequentially treating spleen cells first with complement-fixing monoclonal antibodies directed against with thy 1.2 antigens of T cells and second with complement to lyse any T cells present (New England Nuclear, Boston, Ma.). The cells so treated are thereafter grown with or without 0.1 ml of 0.1 percent (v/v) SRBC as immunogen in serum-containing media further containing incremental amounts of a guanosine analog derivative ranging in amount from zero through $10^{-4}$ molar Direct PFC to SRBC are determined 4 days thereafter.

Mice

CBA/CaJ mice, 8–16 weeks of age, are purchased from the Jackson Laboratory, Bar Harbor, Me. A breeding nucleus of CBA/N mice is provided by the Animal Production Section, National Institutes of Health, Bethesda, Md. All mice are maintained on Wayne Lab Blox F6 pellets (Allied Mills, Inc., Chicago, Ill.) and chlorinated water acidified with HCl to a pH value of 3.0.

Cell preparations

Spleen and thymus cell suspensions are prepared as described in Goodman et al., *J. Immunol.*, 121:1905 (1978). B cell-enriched populations are prepared by treating $10^8$ spleen cells with a 1:1000 dilution of monoclonal anti-thy 1.2 antibody (New England Nuclear, Boston, Ma.) for 30 minutes at 4° C. Treated cells are centrifuged at 280xgravity for 10 minutes, antibodies are removed, and the cells are resuspended in a 1:6 dilution of CBA RBC-absorbed guinea pig complement at 37° C. for 45 minutes. Cells are then washed and cultured as described before.

Injections

Mice are injected i.p. with a solution containing 50 ug of TNP-BSA. Within about 30 minutes of the immunizing injection, two groups of six mice eachaalso receive 0.2 ml i.p. injections of a guanosine analog derivative of the invention in 100 percent sesame oil, or 2 percent (v/v) sesame oil sonicated in normal saline, with the guanosine analog derivative being present at 5 mg/ml. A third group of six mice receive the immunization but no guanosine analog derivative. Anti-TNP-BSA antibody titers are thereafter determined using standard techniques.

The present invention has been described with respect to preferred embodiments. It will be clear to those skilled in the art that modifications and/or variations of the disclosed subject matter can be made without departing from the scope of the invention set forth herein.

What is claimed is:

1. A method for enhancing the antigen-specific humoral immune response of B lymphocytes in a test animal comprising the steps of:

contacting B lymphocytes with a composition containing a diluent amount of a physiologically tolerable carrier with an immune response-enhancing effective amount of an active ingredient that is a guanosine analog derivative whose structure conforms to that of the formula

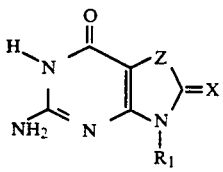

wherein

Z is O or S;

X is O or S;

$R_1$ is 1'-beta-D-ribofuranosidyl and its $C_1$–$C_6$ alkyl, $C_1$–$C_6$ alkanoyl, $C_1$–$C_6$ alkylidene, benzyl and benzoyl derivatives, and the pharmaceutically acceptable non-toxic, base addition salts of said guanine analog derivative; and maintaining said contact for a time period sufficient to said B lymphocytes to enhance their response.

2. The method according to claim 1 wherein said guaosine analog derivative is 7-deaza-7-oxa-8-thio-9,1'-beta-D-ribofuranosidyl guanine.

3. The method according to claim 1 wherein said guanosine analog derivative is 7-deaza-7-oxa-8-oxo-9,1'-beta-D-ribofuranosidyl guanine.

4. A guanosine analog derivative whose structure conforms to that of the formula

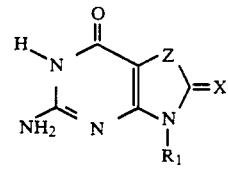

wherein

Z is O;

X is O or S; and $R_1$ is 1'-beta-D-ribofuranosidyl and its O-substituted $C_1$–$C_6$ alkyl, $C_1$–$C_6$ alkanoyl, 2',3'-$C_1$–$C_6$ alkylidene, benzyl and benzoyl derivatives, and the pharmaceutically acceptable non-toxic, base addition salts of said guanosine analog.

5. A guanosine analog derivative whose structure conforms to that of the formula

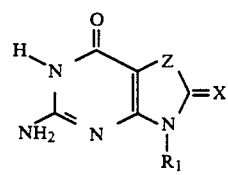

wherein

Z is O;

X is O or S; and $R_1$ is 1'-beta-D-ribofuranosidyl and the pharmaceutically acceptable non-toxic, base addition salts of said guanosine analog.

6. 7-Deaza-7-oxa-8-oxo-9-(1'-beta-D-ribofuranosidyl)guanine.

7. 7-Deaza-7-oxa-8-oxo-9-(1'-beta-D-2'-deoxyribofuranosidyl)guanine.

* * * * *

UNITED STATES PATENT AND TRADEMARK OFFICE
CERTIFICATE OF CORRECTION

PATENT NO. : 5,166,141

DATED : November 24, 1992

INVENTOR(S) : Michael G. Goodman et al.

It is certified that error appears in the above-identified patent and that said Letters Patent is hereby corrected as shown below:

Column 1, after the title and before the heading "CROSS-REFERENCE TO COPENDING APPLICATION", insert the following paragraph:

--This invention was made with government support under Contract Nos. DK 37039 and CA 40186 awarded by the National Institutes of Health. The government has certain rights in the invention.--

Signed and Sealed this

Twenty-fifth Day of April, 1995

*Attest:*

BRUCE LEHMAN

*Attesting Officer*     *Commissioner of Patents and Trademarks*